(12) United States Patent
Rosenzweig et al.

(10) Patent No.: US 8,586,004 B2
(45) Date of Patent: Nov. 19, 2013

(54) OPTIMIZING HYDROGEN GENERATING EFFICIENCY IN FUEL CELL CARTRIDGES

(75) Inventors: Alain Rosenzweig, Saint Maur des Fosses (FR); Andrew J. Curello, Hamden, CT (US); David M. Weisberg, Houston, TX (US)

(73) Assignee: Societe BIC, Clichy Cedex (FR)

( * ) Notice: Subject to any disclaimer, the term of this patent is extended or adjusted under 35 U.S.C. 154(b) by 1287 days.

(21) Appl. No.: 12/089,018

(22) PCT Filed: Oct. 2, 2006

(86) PCT No.: PCT/US2006/038258
§ 371 (c)(1),
(2), (4) Date: Apr. 2, 2008

(87) PCT Pub. No.: WO2007/041403
PCT Pub. Date: Apr. 12, 2007

(65) Prior Publication Data
US 2008/0286621 A1    Nov. 20, 2008

Related U.S. Application Data

(60) Provisional application No. 60/722,410, filed on Oct. 3, 2005.

(51) Int. Cl.
*C01B 3/06* (2006.01)
*H01M 8/06* (2006.01)

(52) U.S. Cl.
USPC .......................................... 423/657; 429/421

(58) Field of Classification Search
USPC ............................ 420/900; 429/421; 423/657
See application file for complete search history.

(56) References Cited

U.S. PATENT DOCUMENTS

| | | | | |
|---|---|---|---|---|
| 4,261,956 | A * | 4/1981 | Adlhart | 422/239 |
| 6,683,025 | B2 * | 1/2004 | Amendola et al. | 502/439 |
| 7,641,889 | B1 * | 1/2010 | Salinas et al. | 423/658.2 |
| 2002/0083640 | A1 | 7/2002 | Finkelshtain et al. | |
| 2004/0052723 | A1 * | 3/2004 | Jorgensen | 423/648.1 |
| 2005/0074643 | A1 | 4/2005 | Adams et al. | |
| 2005/0132640 | A1 | 6/2005 | Kelly et al. | |

FOREIGN PATENT DOCUMENTS

| | | |
|---|---|---|
| JP | 2005-63698 | 3/2005 |
| JP | 2005154232 A | 6/2005 |
| JP | 2005284395 A | 10/2005 |
| WO | 03006150 A1 | 1/2003 |

OTHER PUBLICATIONS

International Search Report and Written Opinion issued in connection with international application PCT/US2006/038258 on Sep. 4, 2007.

(Continued)

*Primary Examiner* — Wayne Langel
*Assistant Examiner* — Syed Iqbal
(74) *Attorney, Agent, or Firm* — The H.T. Than Law Group

(57) ABSTRACT

The present invention involves modifying certain characteristics of solid and aqueous chemical metal hydride fuels to increase the efficiency of hydrogen generation and/or to reduce the problems associated with such conventional hydride fuel sources. The present invention also relates to an apparatus (10) usable with the release of hydrogen from hydride-water fuel cells in which both the borohydride (110) and the water (210) components are in flowable or liquid form.

15 Claims, 1 Drawing Sheet

(56) References Cited

OTHER PUBLICATIONS

Machine translation of JP 2005-63698 to Mikajiri Kazumi, Mar. 10, 2005.

Machine Translation of JP 2005284395 A to Furukawa, Oct. 13, 2005.

Machine Translation of JP 2005154232 to Hironobu et al., Jun. 16, 2005.

* cited by examiner

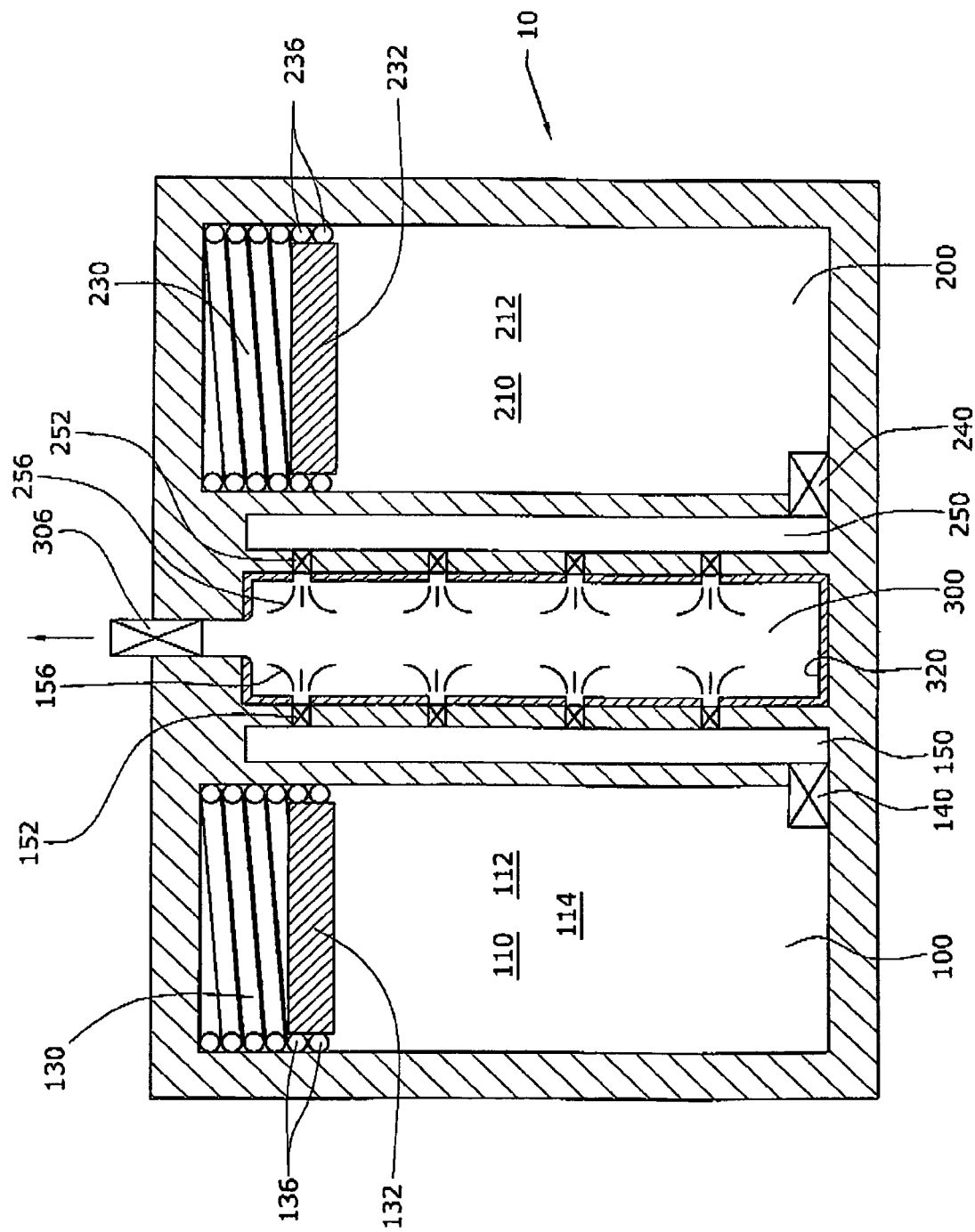

OPTIMIZING HYDROGEN GENERATING EFFICIENCY IN FUEL CELL CARTRIDGES

BACKGROUND OF THE INVENTION

Fuel cells are devices that directly convert chemical energy of reactants, i.e., fuel and oxidant, into direct current (DC) electricity. For a number of applications, fuel cells can be more efficient than conventional power generation, such as combustion of fossil fuel, as well as portable power storage, such as lithium-ion batteries.

In general, fuel cell technology includes a variety of different fuel cells, such as alkali fuel cells, polymer electrolyte fuel cells, phosphoric acid fuel cells, molten carbonate fuel cells, solid oxide fuel cells and enzyme fuel cells. Today's more important fuel cells can be divided into several general categories, namely (i) fuel cells utilizing compressed hydrogen ($H_2$) as fuel; (ii) proton exchange membrane (PEM) fuel cells that use alcohols, e.g., methanol ($CH_3OH$), metal hydrides, e.g., sodium borohydride ($NaBH_4$), hydrocarbons, or other fuels reformed into hydrogen fuel; (iii) PEM fuel cells that can consume non-hydrogen fuel directly or direct oxidation fuel cells; and (iv) solid oxide fuel cells (SOFC) that directly convert hydrocarbon fuels to electricity at high temperature.

Compressed hydrogen is generally kept under high pressure and is therefore difficult to handle. Furthermore, large storage tanks are typically required and cannot be made sufficiently small for consumer electronic devices. Conventional reformat fuel cells require reformers and other vaporization and auxiliary systems to convert fuels to hydrogen to react with oxidant in the fuel cell. Recent advances make reformer or reformat fuel cells promising for consumer electronic devices. The most common direct oxidation fuel cells are direct methanol fuel cells or DMFC. Other direct oxidation fuel cells include direct ethanol fuel cells and direct tetramethyl orthocarbonate fuel cells. DMFC, where methanol is reacted directly with oxidant in the fuel cell, has promising power application for consumer electronic devices. SOFC convert hydrocarbon fuels, such as butane, at high heat to produce electricity. SOFC requires relatively high temperatures in the range of 1000° C. for the fuel cell reaction to occur.

Another type of liquid fuel is hydrazine, which can be anhydrous or in its monohydrate form. Hydrazine is soluble in water and decomposes to form hydrogen in the presence of water, as follows:

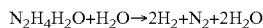

The chemical reactions that produce electricity are different for each type of fuel cell. For DMFC, the chemical-electrical reaction at each electrode and the overall reaction for a direct methanol fuel cell are described as follows:

Half-reaction at the anode:

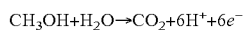

Half-reaction at the cathode:

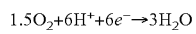

The overall fuel cell reaction:

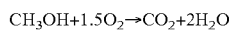

Due to the migration of the hydrogen ions ($H^+$) through the PEM from the anode to the cathode and due to the inability of the free electrons ($e^-$) to pass through the PEM, the electrons flow through an external circuit, thereby producing an electrical current through the external circuit. The external circuit may be used to power many useful consumer electronic devices, such as mobile or cell phones, calculators, personal digital assistants, laptop computers, and power tools, among others.

DMFC is discussed in U.S. Pat. Nos. 5,992,008 and 5,945,231, which are incorporated by reference herein in their entireties. Generally, the PEM is made from a polymer, such as Nafion® available from DuPont, which is a perfluorinated sulfonic acid polymer having a thickness in the range of about 0.05 mm to about 0.50 mm, or other suitable membrane. The anode is typically made from a Teflonized carbon paper support with a thin layer of catalyst, such as platinum-ruthenium, deposited thereon. The cathode is typically a gas diffusion electrode in which platinum particles are bonded to one side of the membrane.

In another direct oxidation fuel cell, borohydride fuel cell (DBFC) reacts as follows:

Half-reaction at the anode:

$$BH_4- + 8OH- \rightarrow BO_2- + 6H_2O + 8e-$$

Half-reaction at the cathode:

$$2O_2 + 4H_2O + 8e- 8OH-$$

Chemical metal hydride fuels are promising due to their relatively higher energy density, i.e., amount of hydrogen per mass or volume of fuel. In a chemical metal hydride fuel cell, sodium borohydride is reformed and reacts as follows:

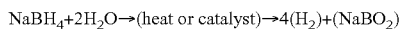

Half-reaction at the anode:

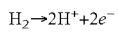

Half-reaction at the cathode:

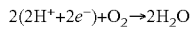

Suitable catalysts for this reaction include platinum, ruthenium, and other metals. The hydrogen fuel produced from reforming sodium borohydride is reacted in the fuel cell with an oxidant, such as $O_2$, to create electricity (or a flow of electrons) and water byproduct. Sodium borate ($NaBO_2$) byproduct is also produced by the reforming process. A sodium borohydride fuel cell is discussed in U.S. Pat. No. 4,261,956, which is incorporated by reference herein in its entirety.

Despite the potential benefits of higher energy density, chemical metal hydride fuels have not achieved the desired energy density for use with portable electronic devices including the amount of hydrogen that can be released from the fuel. One of the reasons for this in sodium borohydride fuel cells is that, in practice, substantially more water is needed to realize complete oxidation of all of the solid sodium borohydride than stoichiometry would indicate. Hence, there remains a need to increase the energy density and maximize the release of hydrogen from chemical metal hydride fuels.

SUMMARY OF THE INVENTION

One aspect of the present invention relates to a hydrogen-generating fuel composition comprising: (1) a fuel component that comprises (a) a metal hydride and (b) a liquid that is not reactive with the metal hydride in the absence of a stabilizing agent; and (2) a liquid reactant component that comprises (a) water, (b) optionally an additive to lower the pH of the liquid reactant component, (c) optionally a transition metal or rare earth metal catalyst, and (d) optionally a phase adjustment additive, wherein the fuel component is reactive with the liquid reactive component to release hydrogen gas. In one preferred embodiment, the non-reactive liquid (1b) comprises ammonia, hydrazine, tetraethyleneglycoldimethylether, triethyleneglycoldimethylether, or a combination thereof.

Another aspect of the invention relates to a method for increasing the efficiency of a conventional solid metal hydride hydrogen-generating apparatus having a first efficiency comprising the steps of: increasing the surface area of a conventional solid, particulate, palletized, powdered, or agglomerate metal hydride fuel to form an increased surface area solid metal hydride fuel having a second fuel efficiency; providing the increased surface area solid metal hydride in a separate compartment of a hydrogen-generating apparatus; providing a predetermined amount of liquid reactant comprising predominantly water; and adding the liquid reactant to the increased surface area solid metal hydride to create a reaction that generates hydrogen such that the second efficiency is greater than the first efficiency.

In one embodiment, the step of increasing the surface area comprises grinding the conventional metal hydride, which has a first average particle size, to form the increased efficiency metal hydride fuel having a second average particle size that is smaller than the first average particle size. In another embodiment, the step of increasing the surface area further comprises combining the increased efficiency metal hydride particles having a second average particle size with a liquid that is not reactive therewith in the absence of a stabilizing agent. In this embodiment, the increased efficiency metal hydride particles can be partially dissolved in the non-reactive liquid, form a slurry with the non-reactive liquid, or both.

Still another aspect of the invention relates to another method for increasing the efficiency of a conventional solid metal hydride hydrogen-generating apparatus comprising the steps of: dissolving a solid, particulate, palletized, powdered, or agglomerate metal hydride fuel in a liquid that is not reactive with the metal hydride fuel in the absence of a stabilizing agent, so as to form a liquid metal hydride fuel solution; providing the liquid metal hydride fuel solution in a separate compartment of a hydrogen-generating apparatus; providing a predetermined amount of liquid reactant comprising predominantly water; and combining the liquid reactant with the liquid metal hydride fuel solution to create a reaction that generates hydrogen.

Yet another aspect of the invention relates to a hydrogen-generating apparatus adapted for use in the release of hydrogen from hydride-water oxidation reactions in which both the metal hydride fuel and the reactant (e.g., water) components are in flowable or liquid form. Advantageously, the hydrogen-generating apparatus contains three compartments: (1) a fuel compartment for housing a flowable metal hydride fuel component, (2) a reactant compartment for housing a liquid reactant component, and (3) a reaction chamber in which the flowable metal hydride fuel component and the liquid reactant component react to form hydrogen gas, which can be used in a fuel cell. In this aspect of the invention, the flowability of the metal hydride fuel component is preferred, because it allows spraying of both fuel and reactant to maximize efficiency through minimizing the reaction surface area and/or through trapping undesirable byproducts of the hydride-water oxidation reaction at the reaction chamber walls.

A preferred metal hydride fuel is a metal borohydride, more preferably sodium borohydride.

BRIEF DESCRIPTION OF THE DRAWING

In the accompanying drawing, which forms a part of the specification, and is to be read in conjunction therewith and in which like reference numerals are used to indicate like parts:

The FIGURE is a cross-sectional schematic view of an apparatus usable with the release of hydrogen from metal hydride fuels.

DETAILED DESCRIPTION OF THE PREFERRED EMBODIMENTS

As illustrated in the accompanying drawing and discussed in detail below, the present invention is directed to methods and compositions capable of maximizing the release of hydrogen from chemical metal hydride fuels, such as sodium borohydride ($NaBH_4$) and water. The present invention is also directed to an apparatus that maximizes the release of hydrogen fuels from a reaction of chemical metal hydride fuels and water.

Suitable known hydrogen generating apparatuses using metal hydride fuels are disclosed in co-pending U.S. application Ser. No. 10/679,756, filed on Oct. 6, 2003; U.S. application Ser. No. 11/067,167, filed on Feb. 25, 2005; U.S. application Ser. No. 11/066,573, filed on Feb. 25, 2005; U.S. Provisional Application No. 60/689,538, filed on Jun. 13, 2005; and U.S. Provisional Application No. 60/689,539, filed on Jun. 13, 2005. The disclosures of all of these references are incorporated by reference herein in their entireties.

Suitable chemical metal hydride fuels include, but are not limited to, hydrides of elements of Groups IA-IVA of the Periodic Table of the Elements and mixtures thereof, such as alkaline or alkali metal hydrides, or mixtures thereof. Other compounds, such as alkali metal-aluminum hydrides (alanates) and alkali metal borohydrides may also be employed. More specific examples of metal hydrides include, but are not limited to, lithium hydride, lithium aluminum hydride, lithium borohydride, sodium hydride, sodium borohydride, potassium hydride, potassium borohydride, magnesium hydride, magnesium borohydride, calcium hydride, and salts and/or derivatives thereof. The preferred hydrides are sodium hydride, sodium borohydride, magnesium borohydride, lithium borohydride, and potassium borohydride, more preferably $NaBH_4$ and/or $Mg(BH_4)_2$.

In solid form, $NaBH_4$, which is typically in the form of relatively large granules or in the solid form of pressed particles, does not hydrolyze in the absence of water, and therefore using anhydrous borohydride improves the shelf life of the cartridge. However, the aqueous form of hydrogen-bearing fuel, such as aqueous $NaBH_4$, typically hydrolyzes readily unless a stabilizing agent is present. Exemplary stabilizing agents can include, but are not limited to, metals and metal hydroxides, such as alkali metal hydroxides, e.g., KOH and/or NaOH. Examples of such stabilizers are described in U.S. Pat. No. 6,683,025, which is incorporated by reference herein in its entirety.

The solid form of the hydrogen-bearing fuel is generally preferred over the aqueous form. In general, solid fuels are thought to be more advantageous than liquid fuels because the aqueous fuels contain proportionally less energy than the solid fuels and the liquid fuels are typically less stable than the solid fuels.

However, one of the problems associated with the aqueous stabilized form of $NaBH_4$ is that the function of the hydroxide stabilizing agent is to inhibit oxidation of the borohydride, which is the desired reaction of the fuel cell cartridge. Additionally, the presence of the KOH stabilizing agent significantly decreases the energy density of the aqueous fuels.

On the other hand, one of the problems associated with the solid forms of $NaBH_4$ (pellet, granule, powder, agglomerate, etc.) is that, during the oxidation of the borohydride by the water, the metaborate ($BO_2^-$) byproduct can appear on the surface of the solid. As the oxidation reaction continues, the metaborate and other forms of borates can tend to form a skin or shell on the surface of the borohydride solid, which can inhibit the borohydride-water oxidation reaction. Furthermore, metaborate and other borate ions can absorb several molecules of water each, reacting with some and chelating with others, which causes the metal hydride oxidation reaction to need more water than the ideal stoichiometric reaction. Also, it is believed that the water must pass through the borate skin and not be chelated by, or reacted with, the borate oxidation byproducts before reaching the borohydride beneath. Even though metaborate and other borate ions are less reactive with water than the borohydride molecules, the borate skin cause the borate-water reaction/chelation step to be rate limiting.

In accordance with the present invention, the aqueous borohydride fuels and the conventional solid forms of borohydride fuels can be modified in one of three ways: (1) by increasing the surface area of the conventional solid forms of the borohydride fuel by grinding the borohydride into smaller particles; (2) by increasing the stability of liquid borohydride without the addition of a stabilizer by replacing the aqueous solution with a non-aqueous, non-borohydride-reactive liquid; and/or (3) by increasing the surface area of the conventional solid forms of the borohydride fuel by adjusting the porosity of the solid borohydride.

In one aspect of the present invention, the surface area of solid borohydride fuel can be increased by further grinding the solid borohydride fuel into smaller particles. Taking a solid borohydride fuel having a first average particle size, the solid borohydride fuel can advantageously be ground into particles having a second average particle size that is not more than about 75%, preferably not more than about 50%, more preferably not more than about 25% of the first average particle size to form an increased surface area solid borohydride fuel. Grinding of the borohydride materials can be accomplished using tools and techniques generally known to those of skill in the art. The increased surface area solid borohydride fuel represents an advantage over conventional solid fuels, because it minimizes the impact of formation of a borate skin that typically coats the conventional solid borohydride fuel during its oxidation by water. The sodium borohydride solids can be ground down to less than about 0.5 mm in size or less, and preferably less than 0.25 mm in size.

Without being bound by theory, the impact of the increased surface area solid borohydride fuel on the borate skin is believed to be at least two-fold. First, increased surface area from decreased particle size can advantageously result in a higher proportion of accessible borohydride with which the water can react before a borate skin forms on the particles. The increased proportion of reactive borohydride sites thus increases the initial hydrogen generation and decreases the amount of unreacted borohydride encapsulated in the borate skin. Second, in addition to increased initial hydrogen generation, increased surface area and decreased particle size are also believed to advantageously increase the total efficiency of the oxidation reaction. In the same way as the smaller particle sizes increase the surface area of borohydride for reaction, they are also believed to increase the surface area of the borate skin, when formed. While the desirability of an increased surface area of borate may be counter-intuitive, increasing the surface area of the borate skin is believed to reduce the skin thickness on each particle, and thus is believed to correspondingly decrease the amount of water the borate skin can consume and/or absorb. Reduced consumption/absorption of water means that there is a reduction from the relatively large empirically observed deviation from theoretical borohydride-water oxidation reaction stoichiometry, and also means that less water needs to be added into the fuel cell to increase the cartridge energy density. As used herein, an exact stoichiometric amount of water reacting with a given amount of metal borohydride fuel represents ideal efficiency, and the greater the necessary deviation from such stoichiometry to substantially complete the metal borohydride oxidation reaction, the lower the efficiency of the system.

In another aspect of the invention, the stability of a liquid borohydride fuel can be greatly increased, as compared to aqueous solutions of borohydride, preferably without the need for a stabilizing additive, by substituting a non-borohydride-reactive liquid phase for the water and stabilizer. The non-borohydride-reactive liquid can be relatively inert with respect to the borohydride-water oxidation reaction and/or can be another liquid fuel that either is also oxidized by water or undergoes oxidation or decomposition in the presence of water to form hydrogen gas, and usually at least one other byproduct. One example of a relatively inert liquid to borohydride is ammonia, preferably substantially anhydrous ammonia. One example of another liquid fuel that can generate hydrogen in the presence of water as a catalyst is hydrazine, which is commercially available in its substantially anhydrous form or as hydrazine monohydrate. Other examples include, but are not limited to tetraethyleneglycoldimethylether and triethyleneglycoldimethylether, available from the Sigma-Aldrich Company. As used herein in relation to the non-borohydride-reactive liquid, the term "substantially" means at least about 99% by weight, preferably at least about 99.5% by weight, more preferably at least about 99.8% by weight, most preferably at least about 99.9% by weight.

The non-borohydride-reactive liquid phase need not completely dissolve the borohydride fuel, although at least partial dissolution is preferred. Partial dissolution of the borohydride in the non-borohydride-reactive liquid can be an alternate method to grinding for decreasing the average particle size of the solid borohydride fuel. Dissolution in the non-borohydride-reactive liquid is a more preferred way to increase surface area, as individual molecules or small groups of associated molecules of the borohydride in solution are accessible to oxidation by the water, which is preferably at least partially miscible with the non-borohydride-reactive liquid.

As used herein, the term "at least partially miscible," as describing a second component in relation to a first component, means that a mixture of the second component and the first component forms a single detectable phase when the weight ratio of the second component to the first component in the mixture is at least about 1:9, preferably at least about 1:4, more preferably at least about 1:2, most preferably at least about 1:1. At least partial miscibility of water in the non-borohydride-reactive liquid is preferred, as it should neither significantly hinder access of the water to the borohydride fuel nor significantly interfere with the borohydride-water oxidation reaction by encapsulation of the borohydride by the non-borohydride-reactive liquid, which would rate-limit the borohydride-water oxidation reaction.

Nevertheless, the non-borohydride-reactive liquid should at least form a slurry with a particulate/powdered borohydride fuel, such that the resulting slurry/solution/colloid is sufficiently flowable to enable liquid transport of the borohydride fuel, e.g., from a fuel compartment into a hydrogen-generating reaction chamber.

In another aspect of the present invention, the surface area of solid borohydride fuel can be increased by adjusting the porosity of solid, agglomerated, pressed, or particulate borohydride fuel. If a pressed particulate or agglomerated particulate form of solid borohydride is used, the porosity of the resulting solid can be increased by adding a non-borohydride-reactive liquid to the particulate borohydride, e.g., to form a paste, and then using the combination as an increased porosity borohydride fuel. Taking a conventional solid borohydride fuel having a first porosity, the addition of a non-borohydride-reactive liquid to form the increased porosity solid borohydride fuel can advantageously result in the increased porosity solid borohydride fuel having a second porosity that is at least about 10% greater than, preferably at least about 25% greater than, more preferably at least about 50% greater than, and in some cases at least about 75% greater than the first porosity. The amount of non-borohydride-reactive liquid added need not render the borohydride-liquid mixture flowable, as discussed above. Nevertheless, enough non-borohydride-reactive liquid can be added either to achieve the aforementioned porosity increase or to achieve an increased surface area of the increased porosity solid borohydride fuel that can advantageously be at least about 25% greater than, preferably at least about 50% greater than, more preferably at least about 75% greater than, most preferably at least about 100% greater than the surface area of the conventional solid borohydride fuel. Both porosity and surface area can be measured using standard tools and techniques available to those of skill in the art. Because of the relatively high level of reactivity of the borohydride fuel, determination of porosity and/or surface area values may rely in part on nuclear imaging methods using, e.g., one or more components having $^2H$, $^{10}B$, $^{11}B$, $^{12}C$, $^{13}C$, and/or $^{15}N$ atoms as part of their molecular structure.

As with the ground particulate borohydride, the increased porosity solid borohydride fuel represents an advantage over conventional solid fuels, because its increased surface area minimizes the impact of formation of a borate skin that typically forms on the surface of conventional solid borohydride fuels during their direct oxidation by water.

Typically, a liquid reactant component reacts with the chemical metal hydride fuel to generate hydrogen. As indicated above and in the formulation below, water, which typically comprises the majority of the reactant component, may react with the borohydride fuel, in this case $NaBH_4$, to generate hydrogen according to the following reaction scheme:

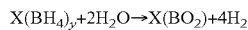

$$X(BH_4)_y + 2H_2O \rightarrow X(BO_2) + 4H_2$$

where X includes, but is not limited to, any Group IA or Group IIA metals such as Na, Mg, Li, K, or the like, or a combination thereof, and where y is a number that represents the valence of X.

In some embodiments, in addition to water, the reactant can also include optional additives to reduce or to increase the pH of the solution. Under certain circumstances, the pH of the reactant can be controlled to determine the speed at which hydrogen is produced. For example, additives that reduce the pH of the reactant typically result in a higher rate of hydrogen generation. Such additives can include, but are not limited to, acids such as hydrochloric acid (HCl), hydrofluoric acid (HF), nitric acid ($HNO_3$), acetic acid ($HC_2H_3O_2$), sulfuric acid ($H_2SO_4$), citric acid ($H_3C_6H_5O_7$), carbonic acid ($H_2CO_3$), phosphoric acid ($H_3PO_4$), oxalic acid ($H_2C_2O_4$), partially ionized salts thereof, and combinations thereof. Conversely, additives that raise the pH, e.g., basic compounds, can lower the reaction rate, in some cases to the point where almost no hydrogen evolves. The solution of the present invention can advantageously have any pH value less than about 7, such as a pH of from about 0.01 to about 6, or more preferably from about 0.1 to about 3.0.

In some embodiments, in addition to water, the reactant can also optionally include a catalyst that can initiate and/or facilitate the production of hydrogen gas, for example, by increasing the rate at which the reactant component reacts with the fuel component. When present, the optional catalyst can be utilized in any shape, size, or state (e.g., liquid, solid, or vapor) capable of promoting the desired reaction. For example, the catalyst can be small enough to form a powder or it can be as large as the reaction chamber. When present, the catalyst can be located inside the reaction chamber or proximate to the reaction chamber, as long as at least one of the reactant and the fuel component comes into contact with the catalyst.

The catalyst may include one or more transitional metals from Group VIIIB of the Periodic Table of the Elements. For example, the catalyst may include transitional metals such as iron (Fe), cobalt (Co), nickel (Ni), ruthenium (Ru), rhodium (Rh), platinum (Pt), palladium (Pd), osmium (Os) and iridium (Ir). Additionally, transitional metals in Group IB, i.e., copper (Cu), silver (Ag) and gold (Au), and in Group IIB, i.e., zinc (Zn), cadmium (Cd) and mercury (Hg), may also be used in the catalyst of the present invention. The catalyst may also include other transitional metals and/or rare earth metals including, but not limited to, scandium (Sc), titanium (Ti), vanadium (V), chromium (Cr) and manganese (Mn). Transition metal catalysts useful in the present invention are described in U.S. Pat. No. 5,804,329, the disclosure of which is incorporated by reference herein in its entirety.

Some of the optional catalysts can generically be defined by the following formula:

$$M_aX_b$$

wherein M is a transition or rare earth metal, X is a moiety bound covalently, ionically, or through hydrogen-bonding to the metal, and "a" and "b" are integers from 1 to 6 as needed to balance the valence of M.

Suitable transitional metal cations can include, but are not limited to, iron (II) ($Fe^{2+}$), iron (III) ($Fe^{3+}$), cobalt ($Co^{2+}$), nickel (II) ($Ni^{2+}$), nickel (III) ($Ni^{3+}$), ruthenium (III) ($Ru^{3+}$), ruthenium (IV) ($Ru^{4+}$), ruthenium (V) ($Ru^{5+}$), ruthenium (VI) ($Ru^{6+}$), ruthenium (VIII) ($Ru^{8+}$), rhodium (III) ($Rh^{3+}$), rhodium (IV) ($Rh^{4+}$), rhodium (VI) ($Rh^{6+}$), palladium ($Pd^{2+}$), osmium (III) ($Os^{3+}$), osmium (IV) ($Os^{4+}$), osmium (V) ($Os^{5+}$), osmium (VI) ($Os^{6+}$), osmium (VIII) ($Os^{8}$), iridium (III) ($Ir^{3+}$), iridium (IV) ($Ir^{4+}$), iridium (VI) ($Ir^{6+}$), platinum (II) ($Pt^{2+}$), platinum (III) ($Pt^{3+}$), platinum (IV) ($Pt^{4+}$), platinum (VI) ($Pt^{6+}$), copper (I) ($Cu^+$), copper (II) ($Cu^{2+}$), silver (I) ($Ag^+$), silver (II) ($Ag^{2+}$), gold (I) ($Au^+$), gold (III) ($Au^{3+}$), zinc ($Zn^{2+}$), cadmium ($Cd^{2+}$), mercury (I) ($Hg^+$), mercury (II) ($Hg^{2+}$), and the like.

Suitable X moieties can include, but are not limited to, hydride ($H^-$), fluoride ($F^-$), chloride ($Cl^-$), bromide ($Br^-$), iodide ($I^-$), oxide ($O^{2-}$), sulfide ($S^{2-}$), nitride ($N^{3-}$), phosphide ($P^{4-}$), hypochlorite ($ClO^-$), chlorite ($ClO_2^-$), chlorate ($ClO_3^-$), perchlorate ($ClO_4^-$), sulfite ($SO_3^{2-}$), hydrogen sulfite ($HSO_3^-$), sulfate ($SO_4^{2-}$), hydrogen sulfate ($HSO_4^-$), hydroxide ($OH^-$), cyanide ($CN^-$), thiocyanate ($SCN^-$), cyanate ($OCN^-$), peroxide ($O_2^{2-}$), hydroperoxide ($HOO^-$), manganate ($MnO_4^{2-}$), permanganate ($MnO_4^-$), chromate ($CrO_4^{2-}$), dichromate ($Cr_2O_7^{2-}$), carbonate ($CO_3^{2-}$), hydrogen carbonate ($HCO_3^-$), phosphate ($PO_4^{2-}$), hydrogen phosphate ($HPO_4^-$), dihydrogen phosphate ($H_2PO_4^-$), phosphite ($PO_3^{2-}$), hydrogen phosphite ($HPO_3^-$), hypophosphite ($PO_2^-$), aluminate ($Al_2O_4$), arsenate ($AsO_4^{3-}$), nitrate ($NO_3^-$), nitrite ($NO_2^-$), acetate ($CH_3COO^-$), oxalate ($C_2O_4^{2-}$), alkoxide ($CH_3(CH_2)_nO^-$, where n is a whole number from 0 to about 19, and the like.

In some embodiments, also included in the reactant and/or in the reaction chamber can be an optional additive that is capable of substantially preventing the freezing of or reducing the freezing point of the reactant component and/or the fuel component. In one embodiment, the optional additive can be an alcohol-based composition, such as an anti-freezing agent. In another embodiment, the optional phase adjustment additive includes, but is not limited to, methanol ($CH_3OH$), ethanol ($CH_3CH_2OH$), propanol (e.g., 1-propanol ($CH_3CH_2CH_2OH$) or 2-propanol ($CH_3CHOHCH_3$)), butanol ($CH_3(CH_2)_3OH$), pentanol ($CH_3(CH_2)_4OH$), hexanol ($CH_3(CH_2)_5OH$), and the like. Optional additives for altering the vapor point or boiling point of the components can also be used.

Another aspect of the invention relates to a suitable hydrogen gas-generating apparatus usable with liquid oxidant/reactant components and flowable fuel components, as described herein, a cross-section of which apparatus is shown in the FIGURE. The hydrogen generating apparatus or fuel cell cartridge 10, contains within its sidewalls three compartments: (1) fuel compartment 100 for housing flowable metal hydride fuel component 110, (2) reactant compartment 200 for housing liquid reactant component 210, and (3) reaction chamber 300. In order to utilize the hydrogen gas formed during the fuel-reactant oxidation reaction, reaction chamber 300 is configured to be connected to a fuel cell (not shown) via hydrogen valve 306 and a fuel conduit.

Flowable metal hydride fuel component 110 in fuel compartment 100 contains metal hydride and liquid 112 that is not reactive with the metal hydride. The metal hydride can, in some embodiments, be substantially dissolved in liquid 112. In other embodiments, where the metal hydride is only partially dissolved in liquid 112 or is substantially insoluble in liquid 112, flowable metal hydride fuel component 110 can comprise a slurry 114 of metal hydride particles in non-hydride-reactive liquid 112. Fuel compartment 100 is preferably pressurized, at least in part resulting from spring-biased piston 132, which is sealingly and slidingly disposed, initially, at or near the top of fuel compartment 100. Spring-biased piston 132 can slide along the sidewalls of fuel compartment 100 by means of sliders 136, which can be elastomeric wipers, gaskets, o-ring seals or the like, capable of allowing piston 132 to slide sealingly along the walls of fuel compartment 100. Piston 132 is biased by spring 130, which may be any appropriate spring known in the art and fixedly mounted onto the top wall of fuel compartment 100 as shown, or piston 132 can be biased by compressed gas, compressed foam, or liquid hydrocarbons. In some embodiments, the top wall of fuel compartment 100 may be coterminous with a sidewall of hydrogen generating apparatus 10. Preferably, piston 132 is sealed with a lubricating sealing material (not shown), such as petroleum jelly, although other sealing components such as o-rings or gaskets may be used. Biasing spring 130 advantageously provides a force, F, on piston 132 so that flowable metal hydride fuel component 110 can be forced through pressure valve 140 toward reaction chamber 300, when desired.

Another aspect of the invention relates to a suitable hydrogen gas-generating apparatus usable with liquid oxidant/reactant components and flowable fuel components, as described herein, a cross-section of which apparatus is shown in the FIGURE. The hydrogen generating apparatus or fuel cell cartridge 10 contains within its sidewalls three compartments: (1) fuel compartment 100 for housing flowable metal hydride fuel component 110, (2) reactant compartment 200 for housing liquid reactant component 210, and (3) reaction chamber 300. In order to utilize the hydrogen gas formed during the fuel-reactant oxidation reaction, reaction chamber 300 is configured to be connected to a fuel cell (not shown) via hydrogen valve 306 and a fuel conduit.

Spray nozzle valves 152 can, in one preferred embodiment, be connected to or be a part of any pressure-opened, one-way valve known in the art, such as a check valve or a valve having a pressure responsive diaphragm, which opens when a threshold pressure is reached. In such a case, when reaction chamber 300 is pressurized above a predetermined pressure, e.g., the pressure in fuel compartment 100, with hydrogen gas evolving from the hydride-water oxidation reaction, the pressurized flow of flowable metal hydride fuel component 110 should cease, without any backflow of fuels, reactants or oxidation products inside reaction chamber 300 back through spray nozzle valves 152.

Liquid reactant component 210 in reactant compartment 200 contains a solution 212 comprising predominantly water, optionally an additive to lower pH, optionally a transition metal or rare earth metal catalyst, and optionally a phase adjustment additive. Reactant compartment 200 is preferably pressurized, at least in part resulting from spring piston 232, which is similar to biased piston 132 described above. More specifically, piston 232 is sealingly and slidingly disposed, initially, at or near the top of reactant compartment 200. Spring-biased piston 232 can slide along the sidewalls of reactant compartment 200 by means of sliders 236, capable of allowing sliding of piston 232 sealingly along the walls of reactant compartment 200. Piston 232 is also connected to biasing spring 230 that is fixedly mounted onto the top wall of reactant compartment 200, which may be coterminous with a sidewall of hydrogen generating apparatus 10. Preferably, piston 232 is sealed with a lubricating sealing material (not shown), such as petroleum jelly, although other sealing components such as O-rings or gaskets may be used. Biasing spring 230, which may be any appropriate spring known in the art, advantageously provides a force, F, on piston 232 so that liquid reactant component 210 can be forced through pressure valve 240 toward reaction chamber 300. Spring 230 can be replaced by a pressurized material, such as liquid/gaseous hydrocarbon, e.g., butane, propane, iso-propane, or the like.

Pressure valve 240 separates reactant compartment 200 from reaction chamber reactant conduit 250, which fluidly connects reactant compartment 200 to reaction chamber 300. Pressure valve 240 can be controlled similar to pressure valve 140. Reaction chamber reactant conduit 250 contains multiple spray nozzle valves 252, similar to spray nozzle valves 152. Each spray nozzle valve 252 can be designed to emanate a pattern 256 of droplets, streams, mist, or the like of liquid reactant component 210 multi-directionally into reaction chamber 300. Spray nozzle valves 252 can also preferably be connected to or be a part of one-way valves, such that when reaction chamber 300 is pressurized above a predetermined threshold, e.g., the internal pressure of compartment 200, with hydrogen gas evolving from the hydride-water oxidation reaction, the pressurized flow of liquid reactant component 210 should cease without any backflow of fuels, reactants or oxidation products inside reaction chamber 300 back through spray nozzle valves 252.

Each reactant pattern 256 emanated from reactant spray nozzle valves 252 can advantageously be complementary to each fuel pattern 156 emanated from fuel spray nozzle valves 152, such that flowable metal hydride fuel component 110 flowing out of spray nozzle valves 152 and liquid reactant component 210 flowing out of spray nozzle valves 252 are continually, or at least in regular bursts, freshly exposed to each other, so as to be relatively free from undesirable existing byproducts, such as borates, formed from the hydride-water oxidation reaction.

Since the fuel and the reactant are pressurized to exit through valves 140, 240, cartridge 10 is operable in any orientation. Alternatively, valve 140 or valve 240 or both are omitted so that the pressure inside conduits 150, 250 is the same as the pressure inside compartments 100, 200, respectively. Furthermore, valves 140 and 240, as well as conduits 150 and 250 can be omitted, and spray nozzle valves 152 and 252 are directly exposed to the pressurized liquids in compartments 100 and 200.

Optionally but preferably, a coating layer 320, as shown in the FIGURE, can be disposed on the walls of the reaction chamber 300, at least partially covering surfaces other than fuel spray nozzle valves 152, reactant spray nozzle valves 252, and hydrogen valve 306. Coating layer 320 can advantageously contain or be made from a polymeric material that can trap (meta)borate byproducts from the borohydride-water oxidation reaction. Trapping borates or metaborates can be accomplished by adsorption, covalent reaction, ionic association, strong hydrogen-bonding interactions or the like between borate-attractive functional groups in coating layer 320 and the borate/metaborate byproducts. One example of suitable polymeric materials having borate-attractive functional groups includes poly(vinyl alcohol) (PVOH). Nevertheless, it is believed that most polyhydroxy-functional polymers and copolymers are capable of trapping (meta)borate byproducts. Examples of such polyhydroxy-functional polymers and copolymers include, but are not limited to, poly(vinyl phenol), poly(hydroxyalkyl acrylate)s, poly(hydroxyalkyl alkacrylate)s, and the like, and combinations or copolymers thereof with each other and/or with other comonomers. Optionally, coating layer 320 is pleated or otherwise has its surface area increased to attract more borate byproducts. Alternatively, the reaction chamber can be made from polymers having borate-attractive functional groups.

Hydrogen gas generating apparatus 10 can also be self-regulated, as discussed above in connection with the incorporated-by-reference, commonly-owned patent applications. As the hydride-water oxidation reaction proceeds within reaction chamber 300, hydrogen gas is generated and can build up to form a pressure $P_{300}$ within reaction chamber 300. In reactant compartment 200 and in reaction chamber reactant conduit 250, biasing spring 230 and spring-biased piston 232 exert a pressure $P_{200}$ on liquid reactant component 210, as regulated by spray nozzle valves 252. Similarly, in fuel compartment 100 and in reaction chamber fuel conduit 150, biasing spring 130 and spring-biased piston 132 exert a pressure $P_{100}$ on flowable metal hydride fuel component 110, as regulated by spray nozzle valves 152. Typically, $P_{100}$ and $P_{200}$ should be approximately equivalent, or at least proportional to the respective surface tensions of liquid reactant component 210 and flowable metal hydride fuel component 110. When $(P_{200} \neq P_{100}) >> P_{300}$, components 110 and 210 enter the reaction chamber through the spray nozzle valves and hydrogen gas evolves from the reaction building up pressure within reaction chamber 300. $P_{300}$ can become equivalent to, or exceed, $P_{100}$ and $P_{200}$. At or near which point valves 152, 252, 140 and/or 240 are automatically shut down due to this pressure differential to stop the flow of fuel and reactant from fuel component 110 and liquid reactant component 210, thereby resulting in an effective closing off of valves 152, 252 and a cutting off of the flow of components 110, 210 into reaction chamber 300. One or more, or all of, valves 152, 252, 140 and/or 240 can be spring-based check valves or ball valves that close automatically when $P_{300} \geq P_{100}, P_{200}$. As discussed above, valves 140 and/or 240 are optional. Such check or ball valves are fully disclosed in U.S. patent application Ser. No. 11/067,167 and U.S. Provisional Application Nos. 60/689,538 and 60/689,539, previously incorporated by reference above.

When hydrogen gas is needed by the fuel cell, hydrogen valve 306, as shown in the FIGURE, is opened. Hydrogen valve 306 can be any valve known in the art including, but not limited to, solenoid valve, check valve, etc., and can be opened manually by the user or by the controller controlling the fuel cell or the electronic device. Optionally, a gas-permeable, liquid impermeable membrane (not shown) may be placed in front of hydrogen valve 306. Membrane (not shown) can prevent liquids or byproducts from being transferred to the fuel cell (not shown) via hydrogen valve 306 and fuel conduit (also not shown). Fillers or foam can optionally be used in combination with membrane (not shown) to retain certain liquids or oxidation reaction byproducts and to reduce clogging. Membrane (not shown) may be formed from any liquid impermeable, gas permeable material known to those skilled in the art. Such materials can include, but are not limited to, hydrophobic materials having an alkane group. More specific examples include, but are not limited to: polyethylene compositions, polytetrafluoroethylene, polypropylene, polyglactin (e.g., commercially available under the tradename VICRYL®), lyophilized dural mater, those (co) polymers sold under the tradenames CELGARD® and/or GORE-TEX®, those gas permeable, liquid impermeable materials disclosed in commonly owned, co-pending U.S. patent application Ser. No. 10/356,793 (which is incorporated by reference herein in its entirety), or copolymers or combinations thereof.

In an alternative embodiment, chamber 300 has a surface, such as surface 320, where fuel pattern 156 and reactant pattern 256 are deposited thereon to react to produce hydrogen. The borate byproduct is left on this surface as a layer, and fresh fuel and reactant are deposited on top of the borate byproduct layer to create more fuel and borate byproduct. The advantage of this alternative is that the borate does not encase any fuel, since fresh fuel is deposited on top of the existing borate byproduct. The deposits of fresh fuel and reactant/water can be preceded by a deposit of reactant or water to react or chelate with the existing borate byproduct. Alternatively, a liquid capable of neutralizing borate can be deposited before the deposit of fresh fuel and reactant.

Other suitable gas-generating apparatuses usable with liquid reactant components and non-flowable fuel components described herein are discussed in commonly-owned co-pending U.S. Provisional Application Nos. 60/689,538; 60/689,539; and 60/689,572. The '572 provisional application is also incorporated herein by reference in its entirety.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

We claim:

1. A method for increasing the efficiency of a metal hydride hydrogen-generating cartridge comprising the steps of:
   forming a metal hydride slurry from a solid metal hydride and a liquid that is not reactive therewith in the absence of a stabilizing agent;
   providing the metal hydride slurry in a separate compartment of the hydrogen-generating cartridge;
   providing a predetermined amount of liquid reactant comprising predominantly water;
   pressuring the metal hydride slurry, and contacting the pressurized metal hydride slurry with the liquid reactant to create a reaction that generates hydrogen.

2. The method of claim 1 further comprising the step of grinding the solid metal borohydride, which has a first average particle size to a second average particle size that is smaller than the first average particle size before forming the metal hydride slurry.

3. The method of claim 2, wherein the second average particle size is not more than about 25% of the first average particle size.

4. The method of claim 1, wherein the metal hydride slurry is sufficiently flowable to enable liquid transport thereof.

5. The method of claim 1, wherein the solid metal hydride is partially dissolved in the non-reactive liquid.

6. The method of claim 1, wherein the metal hydride comprises sodium borohydride.

7. The method of claim 2, wherein the step of increasing the surface area comprises grinding the second average particle size is about 0.5 mm or less.

8. The method of claim 7, wherein the second average particle size is about 0.25 mm or less.

9. The method of claim 1, wherein the liquid that is not reactive therewith in the absence of a stabilizing agent is an inorganic liquid.

10. The method of claim 1, wherein the liquid reactant is pressurized before contacting the metal hydride slurry.

11. A method for producing hydrogen comprising the steps of:
dissolving a solid metal hydride fuel in a liquid comprising ammonia, hydrazine, tetraethyleneglycoldimethylether, or triethyleneglycoldimethylether, or a combination thereof, so as to form a liquid metal hydride fuel solution;
providing a predetermined amount of liquid reactant comprising predominantly water; and
combining the liquid reactant with the liquid metal hydride fuel solution to create a reaction that generates hydrogen.

12. The method of claim 11, wherein the liquid metal hydride fuel solution is pressurized before combining with the liquid reactant.

13. The method of claim 11, wherein the liquid reactant is pressurized before contacting the liquid metal hydride fuel solution.

14. The method of claim 11, wherein the metal hydride fuel comprises a metal borohydride.

15. The method of claim 14, wherein the metal borohydride comprises sodium borohydride.

* * * * *